United States Patent [19]
Griffith

[11] Patent Number: 5,196,195
[45] Date of Patent: Mar. 23, 1993

[54] USE OF ARGINASE TO CONTROL NITRIC OXIDE FORMATION

[75] Inventor: Owen W. Griffith, New York, N.Y.

[73] Assignee: Cornell Research Foundation, Inc., Ithaca, N.Y.

[21] Appl. No.: 499,610

[22] Filed: Mar. 27, 1990

[51] Int. Cl.$^5$ .................. A61K 37/54; A61K 37/48
[52] U.S. Cl. .................. 424/94.6; 424/94.1
[58] Field of Search .................. 424/94.6; 435/227

[56] References Cited

U.S. PATENT DOCUMENTS 2,663,668 12/1953 Vrat .................. 424/94.6
2,834,713 5/1958 Robbins .................. 435/227

FOREIGN PATENT DOCUMENTS 2126181 12/1971 Fed. Rep. of Germany ..... 424/94.6

OTHER PUBLICATIONS

Aisaka, K., et al, Biochemical and Biophysic Research Communications, vol. 160, No. 2, pp. 881–886, Apr. 28, 1989.
Iyengar, R., et al, Proc. Natl. Acad. Sci, USA, vol. 84, pp. 6369–6373 Sep. 1987.
Palmer, R. M. J., et al, Nature (London), 333, pp. 664–666, 1988.
Rees, D. D., et al, Proc. Natl. Acad. Sci. USA, vol. 86, pp. 3375–3378, May, 1989.
Aisaka, K., Biochemical and Biophysical Research Communications, 163, No. 2, 710–717 (Sep. 1989).
Hibbs, J. B., et al, The Journal of Immunology, 138, No. 2, 550–565 (1987).
Jackson, J. A., et al, J. Pharmacol. Expt. Ther. 209, 271–274 (1979).
Ko, R. Y. C., et al, J. Biomed. Res. 10, 249–258 (1976).
Olanoff, L. S., et al, J. Biomed. Res. 8, 125–136 (1977).
Savoka, K. V., et al, Biochem. Biophys. Acta 578, 47–53 (1979).
Blethen, S. L., et al, J. Biol. Chem., vol. 243, No. 8, 1671–1677 (1968).
Mitchell, J. A., et al, European Journal of Pharmacology, 182, 573–576 (1990).
Olken, N. M., et al, Biochem. Biophys. Res. Comm., vol. 177, No. 2, 828–833 (Jun. 14, 1991).
Stuehr, D. J., et al, Proc. Natl. Acad. Sci. USA, vol. 88, 7773–7777 (Sep. 1991).
Taylor, H., et al (ed.), Methods in Enzymology, vol. XVIIA, pp. 310–317, 335–340, Academic Press, 1970.
Yui, Y., et al. J. Biol. Chem., vol. 266, No. 19, 12544–12547, 1991.
Greenberg, D. M. in The Enzymes, 2d edition, vol. 4, Boyer, P. D., et al, editors, pp. 257–267, Academic Press, 1960.
Ignarro, L. J., The FASEB Journal, vol. 3, pp. 31–36 (Jan. 1989).

*Primary Examiner*—Jacqueline Stone

[57] ABSTRACT

Reducing plasma levels of endogenous arginine by parenteral administration of arginine depleting agent reduces nitric oxide levels and results in blood pressure increase. Preferably arginase is administered intravenously to raise blood pressure. The arginase can be administered in conjunction with arginine antagonists to potentiate the effect of these. Duration of action and avoidance of antigenicity may be obtained by use in conjunction with a carrier or modifier.

6 Claims, 2 Drawing Sheets

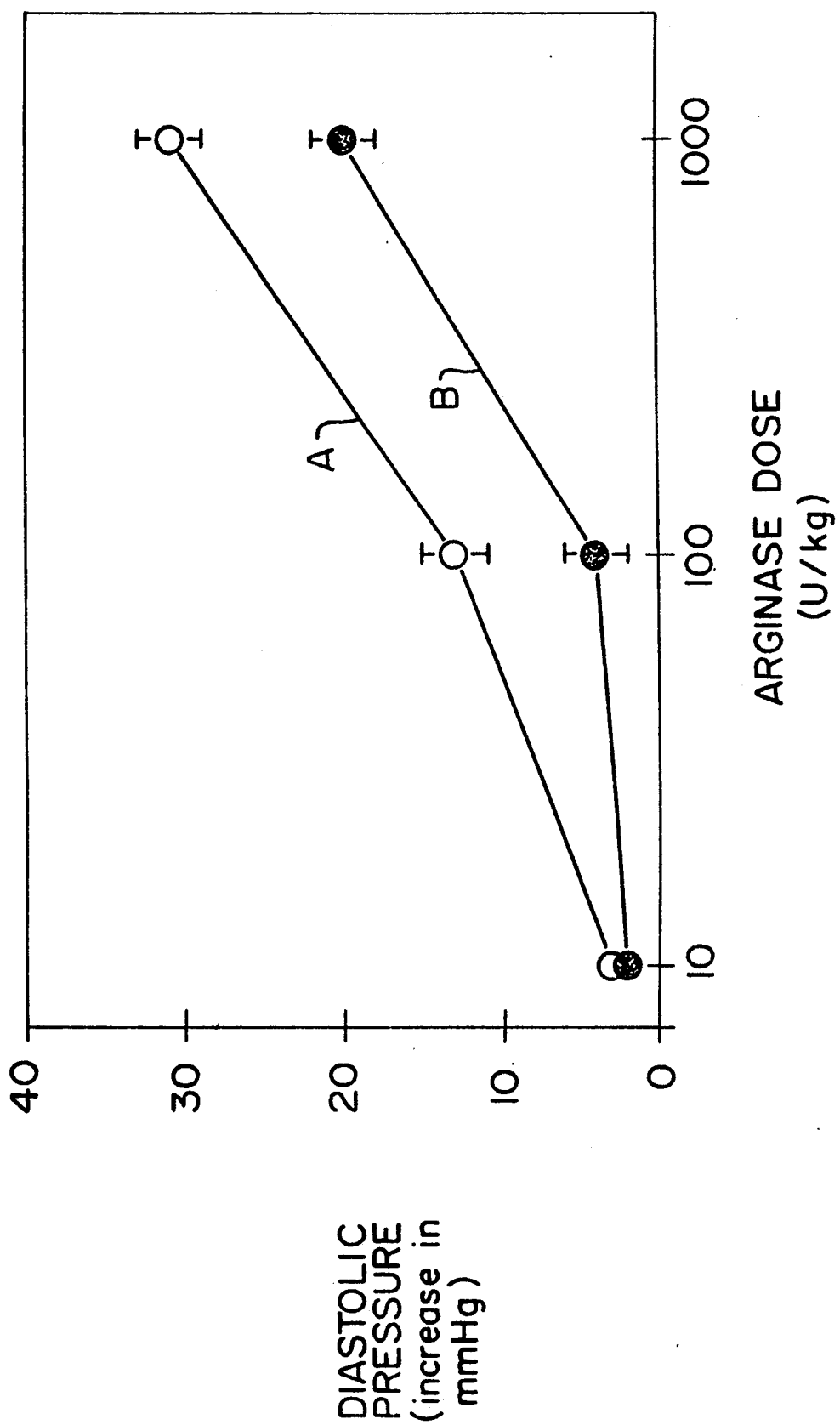

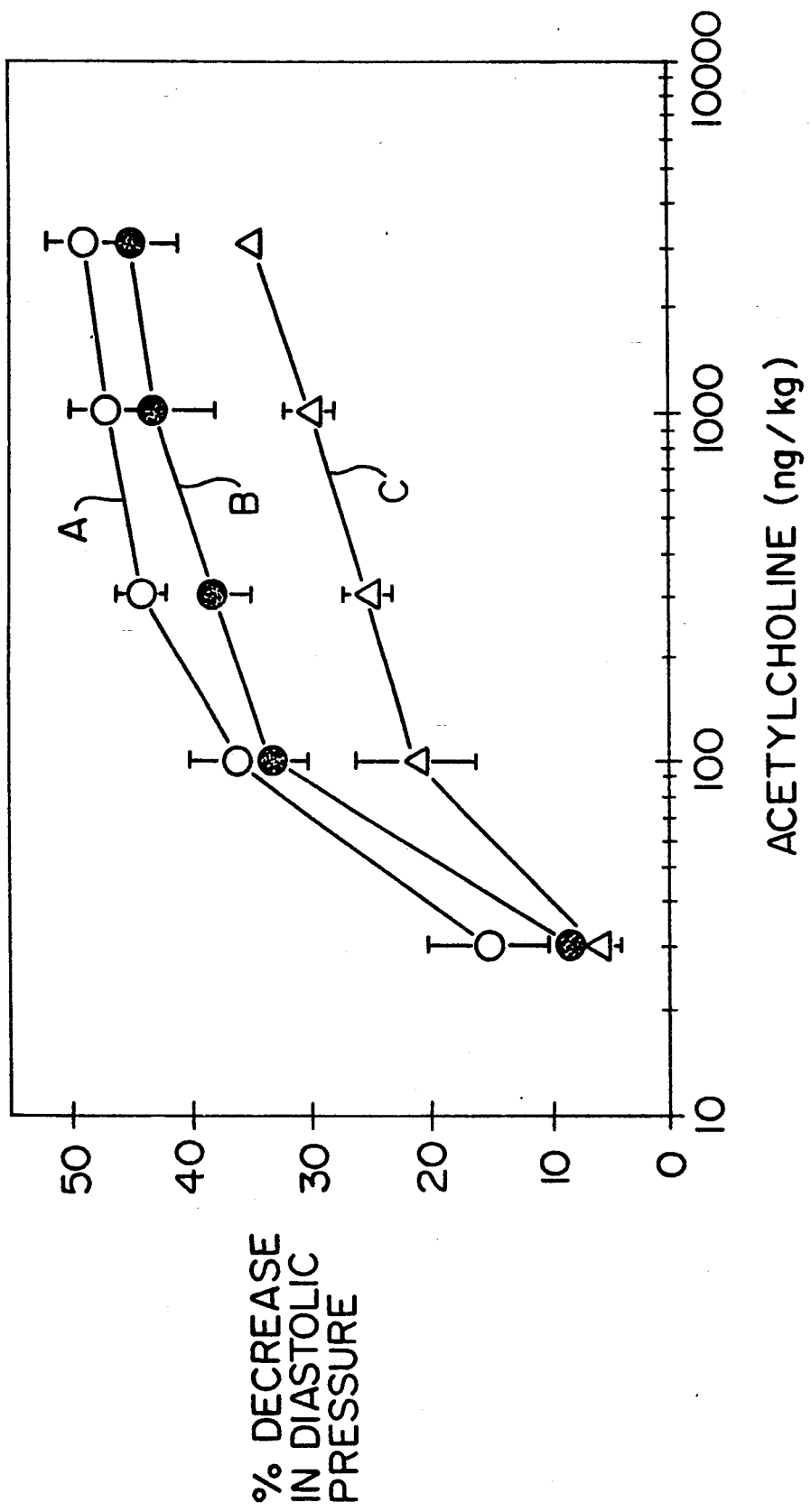

USE OF ARGINASE TO CONTROL NITRIC OXIDE FORMATION

This invention was made at least in part with Government support under National Institutes of Health grant number DK 37116. The Government has certain rights in the invention.

TECHNICAL FIELD

This invention is directed to a novel method of limiting biological nitric oxide formation.

BACKGROUND OF THE INVENTION

For several decades nitroglycerin has been administered to humans as a vasodilating agent in the treatment of cardiovascular disease. By 1987, it had become established that nitroglycerin so administered is converted in the body to nitric oxide which is the pharmacologically active metabolite. Still more recently, nitric oxide has been shown to be formed in endothelial cells from arginine as a normal metabolite which is an important component of endothelium-derived relaxing factor (EDRFs). Nitric oxide, formed by endothelial cells, is taken up by vascular smooth muscle cells and causes relaxation of those smooth muscle cells with concomitant decrease in vascular resistance and blood pressure. It is now widely accepted that many naturally occurring substances which act as physiological or pharmacological vasodilators mediate all or part of their action by stimulating release of EDRFs; these substances include acetylcholine, histamine, bradykinin, leukotrienes, ADP, ATF, substance P, serotonin, thrombin and others. EDRFs are currently being intensively studied as participating in regulation of blood flow and vascular resistance. Incident to such study, a search has been carried out for compounds which inhibit nitric oxide production in the body. One compound discovered for use to obtain this effect is the arginine antagonist $N^G$-methyl-L-arginine (Palmer, R. M. J., et al, Nature (London), 333, pp. 664–666, 1988). Administration of $N^G$-methyl-L-arginine to guinea pigs and rabbits has been shown to increase blood pressure (Aisaka, K., et al, Biochemical and Biophysic Research Communications, Vol. 160, No. 2, pp. 881–886, 1989; Rees, D. D., et al, Proc. Natl. Acad. Sci. USA, Vol. 86. pp. 3375–3378, 1989). Very recently, it has been discovered that arginine antagonists inhibit systemic hypotension (Kilbourn, R. G. et al U.S. Ser. No. 07/406,909) and that a very effective arginine antagonist is physiologically active Ne-amino-arginine (Griffith, O. W., U.S. Ser. No. 07/406,897). It has also been discovered that the duration of the nitric oxide-mediated hypotensive response to acetylcholine is prolonged in animals infused with L-arginine (Aiaska, K., et al, Biochem. Biophys. Res. Commun. 163, 710–717, 1989).

In addition to vascular endothelium, macrophages have also been shown to produce nitric oxide in the body which is a component of their cell killing and/or cytostatic function (Iyengar, R., et al, Proc. Natl. Acad. Sci, USA, Vol. 84, pp. 6369–6373, 1987). It has also been shown in vitro that addition of arginase to cocultivation medium prevents the activated macrophage cytoxic effector mechanism (Hibbs, J. B., et al, The Journal of Immunology, Vol. 138, No. 2, 550–565, 1987).

SUMMARY OF THE INVENTION

It has now been discovered that reducing plasma levels of endogenous arginine limits nitric oxide production in a subject in need of such limitation and that parenteral administration of an arginine depleting agent in an amount reducing the plasma arginine level effects this. The method herein is directed to limiting nitric oxide production in a subject in need of such limiting (whether or not said nitric oxide production has been pathologically stimulated) if said reduction provides a positive result and comprises effecting reduction of plasma level of endogenous arginine. An embodiment of this method comprises parenterally administering an arginine depleting agent in a plasma arginine level reducing amount.

In an important application of the method herein, the nitric oxide production limited is that by endothelial cells and said amount of arginine depleting is such as to cause increase in diastolic blood pressure.

Preferably, the arginine depleting agent is arginase and it is administered intravenously.

In one embodiment herein the arginine depleting agent is administered in a nitric oxide production reducing amount in conjunction with administration of an arginine antagonist in order to reduce the amount of arginine antagonist that would otherwise be administered to inhibit nitric oxide production. In this embodiment the amount of said antagonist administered is 10 to 80% less than a nitric oxide production inhibiting amount of said antagonist in the absence of arginase.

In still another embodiment, the arginine depleting agent is attached to polyethylene glycol or an insoluble support for parenteral administration or is contained in an extracorporeal reactor which is attached to the treated subject's blood supply.

The term "subject" is used herein to mean any mammal, including humans, where nitric oxide formation from arginine occurs.

The methods herein contemplate prophylactic as well as curative use.

BRIEF DESCRIPTION OF THE DRAWINGS

FIG. 1 depicts graphs of Diastolic Pressure vs. Arginase Dose which are results of Example I.

FIG. 2 depicts graphs of % Decrease in Diastolic Pressure vs. Acetylcholine which are results of Example II.

DETAILED DESCRIPTION

The methods herein control endogenous arginine levels to limit nitric oxide production in a subject in need of such limiting. This includes controlling endogenous arginine levels to maintain or obtain nitric oxide production at a level below pathological. In respect to controlling blood pressure, this includes controlling nitric oxide production to a level below that at which pathological decreases in blood pressure occur whether or not nitric oxide production is responsible for said pathological decreases (i.e., the invention includes lowering nitric oxide production to accommodate for a blood pressure decrease which is caused by an agent other than nitric oxide).

As previously indicated, the administration route in the instant invention is parenteral. Parenteral administration includes, for example, intramuscular, intravenous, intraperitoneal, rectal and subcutaneous routes of administration. Preferably, the route of administration is intravenous, for example, at a concentration ranging from 10 to 10000 U/ml in saline or other non-toxic diluent, either as a bolus injection (one administration over 5 seconds or less) for a transient response or as a continuous infusion for a continuous response. Alternatively, continuous response can be obtained by administering arginase attached to polyethylene glycol as either a bolus or continuous infusion or by circulating a portion of the subject's blood flow through an arginase-containing extracorporeal reactor.

The arginine depleting agent is any agent which when administered in a non-toxic amount so changes the character of plasma arginine that is does not function as a nitric oxide metabolite. Suitable arginine depleting agents include, for example, arginase, arginine decarboxylase and arginine deiminase. Arginase is the preferred arginine depleting agent herein. As is well known, it catalyzes the hydrolysis of L-arginine to L-ornithine and urea. Arginase is a commercially available enzyme that is normally present inside cells but not in the plasma. Arginine decarboxylase catalyzes the decarboxylation of arginine. Arginine deiminase converts arginine to citrulline and ammonia.

We turn now to the subjects to be treated by the methods herein.

One group of subjects comprises those with pathologically low blood pressure.

One class within this group are those with idiopathic hypotension.

Another class within this group are those with drug-induced hypotension. In this case coadministration pursuant to the method herein allows use of drugs that otherwise have unacceptable side effects.

Still another class within this group are those suffering from certain forms of shock (including toxic shock syndrome).

Another group of subjects comprises those with immune disorders in which down regulation of nitric oxide formation is advantageous, e.g., in inflammation or auto-immune disorders or in therapeutic immunosuppression for transplant purposes.

Turning now to dosage, such depends on the effect desired and the responsiveness of the individual subject. For example, for raising blood pressure, a blood pressure effective raising amount is administered. For disorders requiring immunosuppression, an immunosuppressive effective amount is administered. Generally, dosages of arginine depleting agent range from 10 to 5000 U/kg for a bolus intravenous injection and from 10 to 1000 U/kg/min for continuous infusion intravenous administration. A unit (U) is defined as the amount of arginine depleting agent necessary to convert 1 micromole of arginine to ornithine and urea per minute at pH of 9.5 at 37° C.

We turn now to the method herein where arginine depleting agent administration is used in conjunction with administration of an arginine antagonist. It has been found herein that the arginine depleting agent potentiates the effect of the arginine antagonist such that the arginine antagonist is administered in am amount 10–80%, preferably 10–30%, less than a nitric oxide production inhibiting amount of said antagonist in the absence of arginase. For this purpose, the arginine depleting agent preferably is arginase administered intravenously in an amount ranging from 10 to 1000 U/kg/min. The arginine antagonist is preferably selected from the group consisting of L-$N^G$-aminoarginine, L-$N^G$-methylarginine and L-$N^G$-nitroarginine. A dosage of 0.1 to 10 mg/kg/minute of L-$N^G$-methylarginine administered intravenously in a bolus injection in conjunction with continuous intravenous infusion of 30 U/kg/minute of arginase has been found effective in raising diastolic blood pressure. The arginine antagonist can also be administered by continuous infusion. Arginase reacts very slowly or not at all with said antagonists so it has no practical effect on negating their functionality.

We turn now to the embodiments where arginase is used in conjunction with a carrier or is administered via an extracorporeal reactor to obtain longer duration of action and avoidance of antigenicity.

In one embodiment where the arginine depleting agent has a longer duration of action and results in a diminished antigenic response by the treated subject, methoxypolyethylene glycol (PEG) is attached to the said agent. The said agent is preferably arginase and the PEG is preferably of 5000 daltons. Arginase and PEG are covalently coupled using 2,4,6-tricloro-s-triazine as described by K. V. Savoca et al. (Biochem. Biophys. Acta 578, 47–53 (1979)); PEG is attached to 50 to 60% of the free amino groups of arginase. Arginase modified in the manner described has a circulating half-life at least 10-fold greater than that of native unmodified arginase when injected intravenously in mice. Sera from mice administered native arginase contains anti-arginase antibodies wherease sera from mice administered PEG-modified arginase does not contain antibodies to either arginase or PEG-modified arginase.

In another embodiment where the arginine depleting agent has a longer duration or action and results in a diminished antigenic response by the treated subject, the said agent is attached to an extracorporeal reactor and the subject's blood is passed through said reactor. The said arginine depleting agent is preferably arginase and the said reactor can be a packed bed of Dacron fibers to which arginase is attached using $\gamma$-aminopropyltriethoxysilane and glutaraldehyde (general method of R. Y. C. Ko., et al, J. Biomed. Res. 10, 249–258 (1976)) or said reactor may be an insoluble carrier matrix of reconstituted bovine collagen containing arginase (general method of L. S. Olanoff, et al, J. Biomed. Res. 8, 125–136 (1977)) or said reactor may be a conventional hollow fiber hemodialyzer to which arginase is attached covalently (general method of J. A. Jackson, et al, J. Pharmacol. Expt. Ther. 209, 271–274 (1979)). In each case the subject's blood is passed through the extracorporeal reactor by means of conventional arteriovenous cannulation wherein blood is removed from the subject through an arterial cannula, passed through the extracorporeal reactor, and then returned to the subject through a venous cannula. Use of an arginine depleting agent in an extracorporeal reactor is preferably employed in normotensive shock-prone subjects in which the necessary cannulations and perfusion apparatus can be placed in service before the subject is overtly hypotensive.

The invention is illustrated in the following examples:

EXAMPLE I

A male Hartley guinea pig weighing about 300 grams is anesthetized with sodium pentobarbital (50 mg/kg i.p.) and a tracheal canula is inserted. The left carotid artery is cannulated and connected to a physiological pressure transducer. Blood pressure tracings are displayed on a physiograph. Diastolic blood pressure is monitored and an intravenous administration by bolus injection (0.2 ml) of 10 U/kg arginase, 100 U/kg arginase, 1000 U/kg arginase (in saline) is given and also these same injections are administered to a guinea pig given L-arginine (30 mg/kg in 0.2 ml saline) and continuously infused with 10 mg/kg/minute of L-arginine in saline (concentration of 120 mg/ml). The results (mean values ± standard error) from studies with 4 guinea pigs are depicted in FIG. 1 where line A (open circles) depicts results where only bolus injections of arginase were used and line B (closed circles) depicts results where bolus injections of arginase were given together with L-arginine. Line A shows that the blood pressure of the guinea pig increases when either 100 U/kg or 1000 U/kg arginase is given as a bolus injection. Line B shows the effect is reduced when L-arginine is given along with the arginase. FIG. 1 (line A) establishes that nitric oxide is continuously formed in the normal guinea pig and is transiently reduced on bolus intravenous administration of 100 U/kg or 1000 U/kg of arginase whereby arginine is removed from the plasma by conversion to onithine and urea by the arginase. FIG. 1 (line B) establishes that the increase in blood pressure is due to removal of plasma arginine by arginase since, if arginine is simultaneously replaced, the increase in blood pressure is less.

EXAMPLE II

Acetylcholine is known to stimulate arginine-dependent nitric oxide formation and thereby cause a fall in blood pressure. Administration of acetylcholine to guinea pigs thus provides a good model for the pathological overproduction of nitric oxide and resultant hypotension characteristic of septic shock and some other forms of shock. It has been shown in studies wherein excess arginine was administered that increased L-arginine availability extends the duration of acetylcholine-induced hypotension (Aisaka, K., et al Biochem. Biophys. Res. Commun. 163, 710–717 1989)). The studies below show that diminished L-arginine availability decreases the extent or duration of acetylcholine-induced hypotension.

The effect of arginase on acetylcholine-mediated hypotension in guinea pigs was determined using the general method described in Aisaka, K., et al, Biochem, Biophys, Res. Commun. 163, 710–717 (1989). The dose of acetylcholine ranged from 30 ng/kg to 3000 ng/kg. The results are shown in FIG. 2. Results with infusion of saline (0.25 ml/min) are depicted in line A (open circles). Results with infusion with 100 U/kg/min arginase in saline (concentration of 4000 U/ml) are depicted in line B (closed circles). Results with infusion with 300 U/kg/min arginase in saline (concentration of 12000 U/ml) are depicted in Line C (open triangles. The results show that the extent of nitric oxide formation is dependent on the level of circulating L-arginine. When nitric oxide production was stimulated to levels simulating those seen in pathological shock conditions (mimicked here by acetylcholine administration), administering arginase depleted circulating arginine and limited the fall in blood pressure.

Constant rate infusion of arginase (100 or 300 U/kg/min, i.v.) without pathological stimulation did not change arterial pressure significantly. Higher doses however do change arterial pressure significantly.

The term "arginine depleting agent" is used herein to mean enzyme, e.g., arginase, used in unmodified state as well as the enzyme modified to obtain longer duration of action, for example, by attachment by covalent coupling to methoxypolyethylene glycol for administration or the enzyme modified for use in an extracorporeal reactor by attachment to Dacron fibers or by covalent bonding to a hollow fiber hemodialyzer or in a collagen matrix.

Many variations of inventive embodiments will be obvious to those skilled in the art. Thus, the inventive embodiments are defined by the claims.

What is claimed is:

1. A method for limiting nitric oxide production in a subject in need of such limiting, said method comprising parenterally administering an amount of a plasma arginine depleting enzyme to effect reduction of plasma level of arginine to a nitric oxide production limiting level.

2. The method of claim 1 wherein the arginine depleting agent is an enzyme selected from the group consisting of arginase, arginine decarboxylase and arginine deiminase.

3. The method of claim 1 wherein said agent is arginase.

4. The method of claim 3 wherein the nitric oxide production limited is that by endothelial cells and said amount of agent is such as to cause increase in diastolic blood pressure.

5. The method of claim 3 wherein the arginase is administered intravenously.

6. The method of claim 3 wherein the arginase is administered in a nitric oxide production reducing amount together with an arginine antagonist, the amount of said antagonist being less than a nitric oxide production inhibiting amount of said antagonist in the absence of arginase.

* * * * *

UNITED STATES PATENT AND TRADEMARK OFFICE
CERTIFICATE OF CORRECTION

PATENT NO. : 5,196,195

DATED : March 23, 1993

INVENTOR(S) : OWEN W. GRIFFITH

It is certified that error appears in the above-identified patent and that said Letters Patent is hereby corrected as shown below:

Claim 2 (column 6, line 34), delete "agent is an" and after "enzyme" insert -- is --.

Claim 3 (column 6, line 37), change "agent" to -- enzyme --.

Claim 4 (column 6, line 41), change "agent" to -- enzyme --.

Signed and Sealed this

Fourteenth Day of December, 1993

*Attest:*

BRUCE LEHMAN

*Attesting Officer*    *Commissioner of Patents and Trademarks*